United States Patent [19]

Sandel

[11] 4,142,632
[45] Mar. 6, 1979

[54] SURGICAL INSTRUMENT HOLDER AND INSTRUMENT TIP PROTECTOR DEVICE

[75] Inventor: Dan S. Sandel, Encino, Calif.

[73] Assignee: Devon Industries, Inc., Northridge, Calif.

[21] Appl. No.: 826,536

[22] Filed: Aug. 22, 1977

Related U.S. Application Data

[63] Continuation-in-part of Ser. No. 740,863, Nov. 4, 1976, abandoned.

[51] Int. Cl.$^2$ ............................ B65D 65/44; A61B 17/06
[52] U.S. Cl. .................................... 206/363; 206/478
[58] Field of Search ............... 206/363, 820, 370, 372, 206/481, 478

[56] References Cited

U.S. PATENT DOCUMENTS

| | | | |
|---|---|---|---|
| 1,901,583 | 3/1933 | Conway | 206/372 |
| 2,788,828 | 4/1957 | Banner | 206/373 |
| 2,830,601 | 4/1958 | Pool | 132/79 R |
| 2,998,880 | 9/1961 | Ladd | 206/210 |
| 3,171,820 | 3/1965 | Volz | 2/97 X |
| 3,330,090 | 7/1967 | Court | 206/363 |
| 3,331,499 | 7/1967 | Jost | 206/210 |
| 3,669,256 | 6/1972 | Jacob | 206/363 |
| 4,039,079 | 8/1977 | Laughton | 206/820 |

Primary Examiner—Herbert F. Ross
Attorney, Agent, or Firm—Poms, Smith, Lande, Glenny & Rose

[57] ABSTRACT

A surgical instrument holder and instrument tip protector device has a base of a non-skid sterilizable material for receiving a surgical instrument positioned thereon and a protective layer formed of a sterilizable resilient material and overlying at least a portion of the base to provide a resilient pouch of sterilizable material into which the tip end of a surgical instrument may be placed for preventing the instrument tip from puncturing a sterile container for the instrument, for preventing damage to the instrument tip, and for protecting a user against injury due to contact with the surgical instrument tip while handling the surgical instrument holder and instrument tip protector device. A plurality of devices in side-by-side integral relation having a protective flap for covering an end of surgical instruments positioned on the devices distal from the instrument tip facilitates an organized assembly of specific surgical instruments to be used in a specific surgical procedure to be prepared, sterilized, and stored for future use as a complete surgical kit. In an alternative embodiment tip protector, pouches are provided at either end of the device for receiving opposite ends of surgical instruments such as a glass syringe.

2 Claims, 11 Drawing Figures

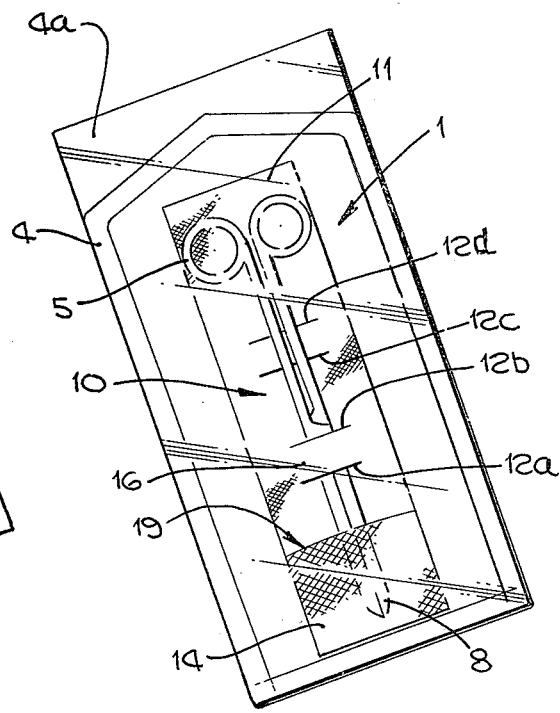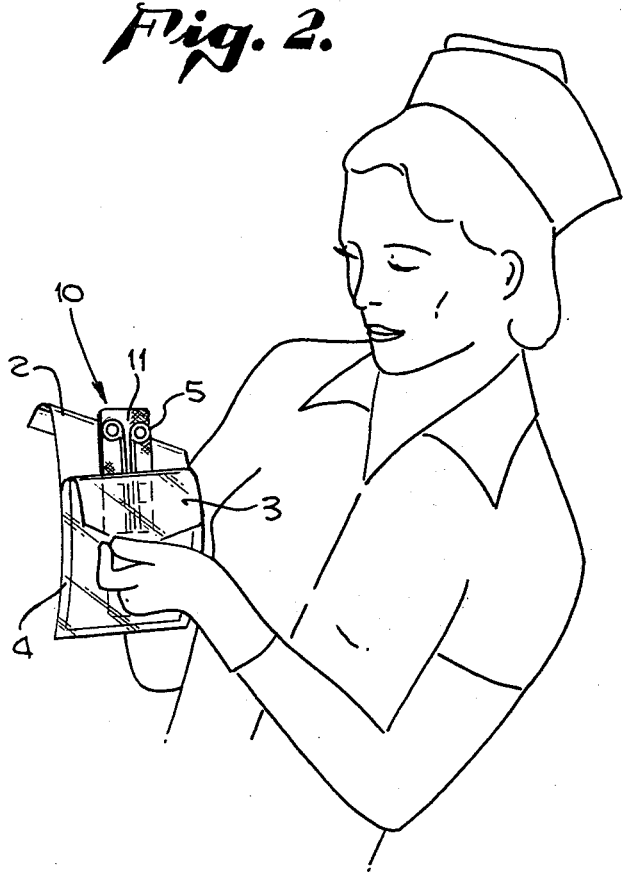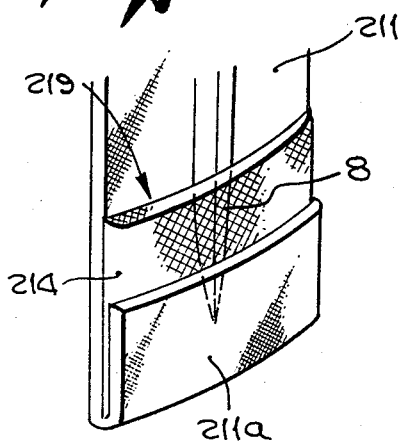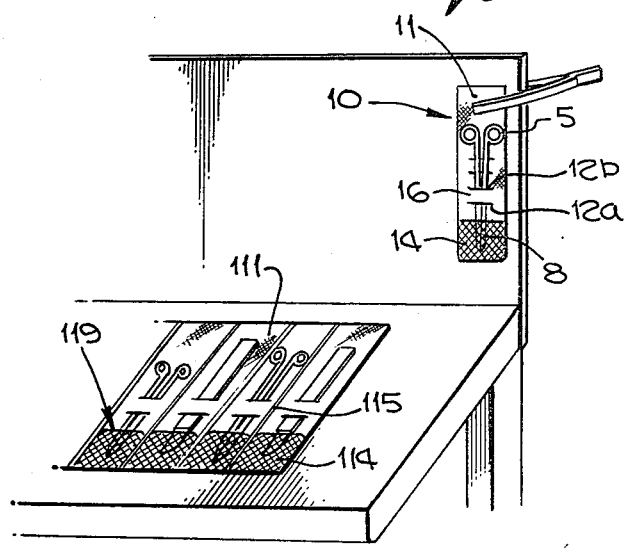

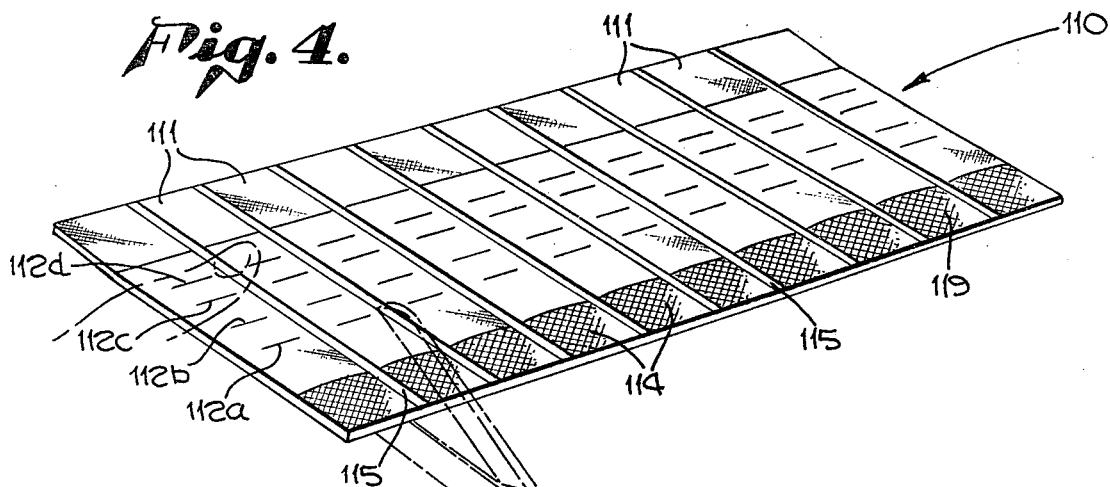
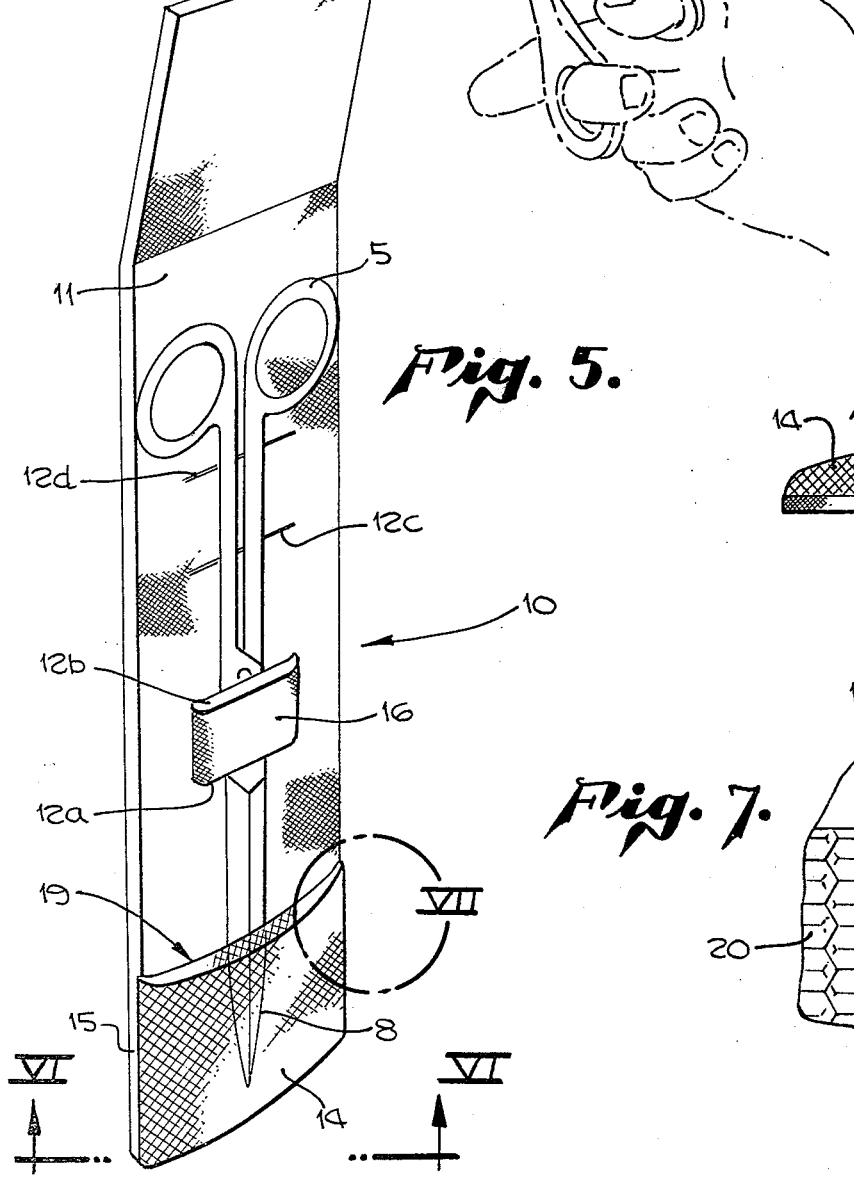
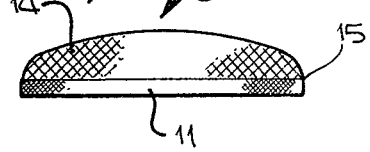
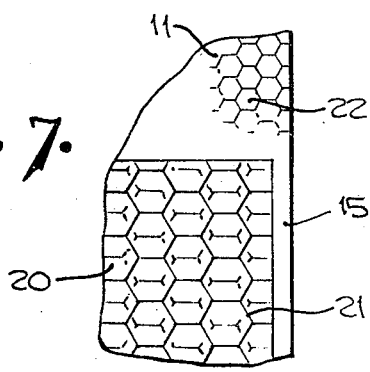

SURGICAL INSTRUMENT HOLDER AND INSTRUMENT TIP PROTECTOR DEVICE

RELATED APPLICATION

This application is a continuation-in-part of my co-pending application Ser. No. 740,863 filed Nov. 11, 1976 entitled "Surgical Instrument Holder and Tip Protector Device" which will be abandoned subsequently in favor of this application.

BACKGROUND OF THE INVENTION

The present invention relates, in general, to devices for holding surgical instruments. Specifically, the present invention relates to surgical instrument holding devices which are sterilizable, which prevent the tips of surgical instruments from becoming damaged, or from injuring surgical and nursing personel during use.

A customary procedure in surgical operating rooms for providing a sterile environment for surgical instruments and for maintaining surgical instruments in a sterile condition until use has been to first, sterilize the instrument in one of many standard procedures, and then to seal the sterile instrument inside a sterile container such as a sterile envelope having at least one transparent surface, to allow operating room personnel to visually identify the surgical instrument contained therein, or, to wrap the instrument in what is commonly known as C.S. wrap, identification of the instruments which are wrapped therein is done by marking the C.S. wrap on the outside.

When the specific surgical instrument within the sterile envelope is required during a surgical procedure, a standard technique for removing the surgical instrument from the sterile envelope is to grasp the portion of the sterile envelope which contains the tip portion of the surgical instrument between the heel portions of the user's hands, to grasp the sterile envelope cover and backing between the thumb and index finger of opposing hands and peel the cover from the backing with a rolling motion of the hands. During this procedure, the tip of the surgical instrument is firmly held between the heels of the user's hands in order to retain it within at least a portion of the sterile envelope.

Due to the inherent nature of the tip portions of surgical instruments which are intended to cut and/or puncture, there has been a strong possibility that the tips of the surgical instruments would cut and/or puncture any non-rigid sterile container such as the sterile envelopes and C.S. wrap being discussed herein. When these sterile containers are punctured, the instrument is no longer considered sterile, the instrument tip may be damaged and require repair, and surgical personel might be injured by the protruding sharpened instrument tip.

Additionally, quite often, the surgical instrument will slide and move within the sterile container to a position which makes the removal of the surgical instrument from the sterile container very difficult. Often, during material handling, this sliding movement will result in the sharpened tip portion of the surgical instrument puncturing or cutting the sterile container, such as the sterile envelope or the C.S. wrap, resulting in the instrument becoming unsterile, as was discussed prior. Both of these eventualities are considered highly undesirable disadvantages.

SUMMARY OF THE INVENTION

It is, therefore, a primary object of the present invention, to disclose and provide a surgical instrument holder and instrument tip protector device which will prevent the surgical instrument from puncturing a non-rigid sterile container such as sterile envelopes and C.S. wrap, which will prevent damage to the tips of surgical instruments and which will protect a user against injury due to contact with the tip of a surgical instrument while handling the device.

It is a further object of the present invention to disclose and provide a surgical instrument holder and instrument tip protector device which will retain surgical instruments inside a non-rigid sterile container and prevent movement of the surgical instrument within the sterile container, prevent the instrument tip from cutting or puncturing the non-rigid sterile container, and, at the same time, enable operating room personel to easily remove the surgical instrument from the non-rigid sterile container.

A further object of the present invention is to disclose and provide an improved surgical instrument holder and instrument tip protector device which will allow visual inspection and identification of the surgical instrument tip while the surgical instrument is being held by the device.

A further object of the present invention is to disclose and provide an improved surgical instrument holder and instrument tip protector device wherein a plurality of devices in side-by-side integral relation may be used together to retain one or more instruments.

A further object of the present invention is to disclose and provide an improved surgical instrument holder and instrument tip protector device made of a non-skid material which will prevent the movement of the device and the surgical instrument positioned thereon from being inadvertently displaced during use.

The improved surgical instrument holder and instrument tip protector device of the present invention comprises a base of a sterilizable material for receiving a surgical instrument positioned thereon and the protective pouch means formed of a sterilizable resilient material overlying at least a portion of the base to provide a resilient pouch of sterilizable material over a tip end of a surgical instrument for preventing the surgical instrument tip from puncturing a non-rigid sterile container such as a sterile instrument or C.S. wrap, for protecting the user against injury due to contact with the tip of the surgical instrument while handling the device and for preventing a surgical instrument from moving within a non-rigid sterile container. The protective pouch means if formed of an opaque reticulated material having a sufficiently coarse pore size to allow visual inspection and identification of the surgical instrument tip through the pouch means. Loop means are formed integrally of the base material for holding a surgical instrument positioned thereon and preventing movement of the surgical instrument with respect to the surgical instrument holder and the instrument tip protector device of the present invention. Further, the device is formed of a non-skid material which will prevent inadvertent movement of the device and an instrument positioned therein during use by surgeons and nursing personel.

A more complete understanding of the improvements in surgical instrument holder and instrument tip protector devices in accordance with the present invention, as well as a recognition of additional objects and advantages therefor will be afforded to those skilled in the art from a consideration of the following detailed description of an exemplary embodiment thereof. Reference will be made to the sheets of drawings which will first be discussed briefly.

BRIEF DESCRIPTION OF THE DRAWINGS

FIG. 1 is a plan view showing the surgical instrument holder and instrument tip protector device of the present invention enclosed in a sterile envelope.

FIG. 2 is a perspective view showing the opening of the sterile envelope by operating room personel wherein the instrument is securely grasped between the heels of the hands and the instrument tip protector device of the present invention prevents injury.

FIG. 3 is a perspective view showing a plurality of surgical instrument holder and instrument tip protector devices in a side-by-side integral relationship for use together and for being separated into individual sections, as well as one section which has been separated and which is clamped in a position for convenient use.

FIG. 4 is a perspective view showing a plurality of surgical instrument holder and instrument tip protector devices in side-by-side integral relationship for use together and for being separated into individual sections, as well as one section which has been separated and which is clamped in a position for convenient use.

FIG. 4 is a perspective view showing a plurality of surgical instrument holder and instrument tip protector devices in side-by-side integral relationship which are being separated into individual sections.

FIG. 5 is a perspective view showing the base of the surgical instrument holder receiving a surgical instrument and the protective means which overlies at least a portion of the base means and provides a resilient layer over a tip end of the surgical instrument.

FIG. 6 is a view through the plane VI—VI of FIG. 5 showing the inter-relationship between the protective resilient layer and the base means of the surgical instrument holder and instrument tip protector device of the present invention.

FIG. 7 is a detail view of the area VII of FIG. 5 showing the relative difference in pore size between the resilient material of the base means and the resilient material of the protective resilient layer, as well as the operational relationship therebetween.

FIG. 8 is a perspective view of a section of an embodiment of the surgical instrument holder and instrument tip protector device of the present invention, showing a zone overlayment of the base means on the protective resilient layer to provide a reinforced sandwich structure.

DETAILED DESCRIPTION OF AN EXEMPLARY EMBODIMENT

Figure 9:
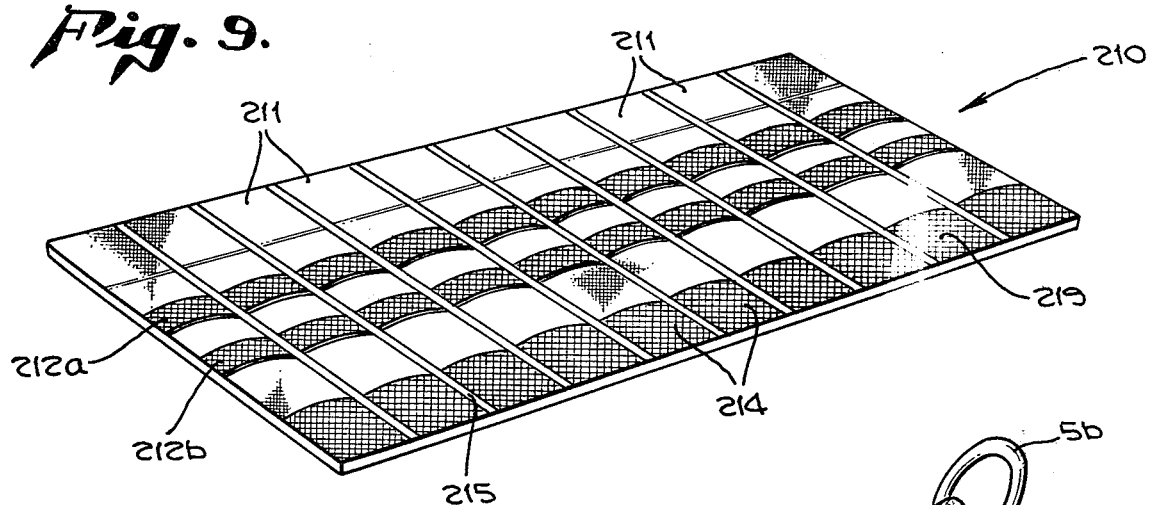
FIG. 9 is a plan view of an alternative exemplary embodiment of surgical instrument holder and instrument tip protector device of the present invention.

Referring first to FIG. 1, the surgical instrument holder and instrument tip protector device of the present invention is shown generally at 10 enclosed within sterile envelope 1. Sterile envelope 1 has backing 2 and transparent cover 3 which are heat-sealed along an edge portion shown generally at 4.

It is common procedure in an operating room for the personel to receive the surgical instrument sealed in non-rigid sterile containers such as the sterile envelope shown at 1 and/or C.S. wrap. The sterile container for the surgical and/or nursing instrument 5 is firmly grasped between the heels of the palm portions of the hands of the person readying the instruments for use, in most cases, a nurse. In grasping the sterile container between the heels of the hands, a portion of the surgical instrument 5 is grasped between the heels of the hands, as is shown in FIG. 2. This should insure a firm retention of the surgical instrument 5 once the container has been opened, but, since the sterile envelope or C.S. wrap is slippery, it is very easy for the instrument to slip and fall to the floor. Further, it exposes the nurse's hands to potential injury by the sharpened tip portion 8 of the surgical instrument.

In the exemplary embodiment shown in FIG. 2, the sterile container comprises a sterile envelope rather than C.S. wrap. To open the envelope once it is firmly held between the heels of the hands, the opposing thumbs are inserted between the transparent cover 3 and backing portion 2 of the sterile envelope in an area which has not been heat-sealed, as is shown generally at 4a. The thumb and index finger of opposing hands grasp the backing portion 2 and the transparent cover 3 firmly and the hands are then rotated such that the backing portion 2 and transparent cover 3 are pulled apart, as shown in FIG. 2. During this entire operation, a portion of the surgical instrument is firmly grasped between the heels of the palm sides of the hands, as is shown in FIG. 2.

The surgical instrument holder and instrument tip protector device 10 comprises base means 11, formed of a sterilizable material, for receiving and holding surgical instruments 5 positioned thereon. Base means 11 is provided with a plurality of holding slots shown at 12a, 12b, 12c and 12d, formed integrally of base means 11 for holding any size instrument placed upon base means 11. As is most clearly shown in FIG. 5, surgical instrument 5 is threaded through adjacent holding slots 12a and 12b and, in effect, creates a retaining loop 16 of base means 11 which is integral with base means 11 and which secures surgical instrument 5 to base means 11.

Protective pouch means in the form of protective resilient layer 14, bonded at 15, formed of a sterilizable resilient material overlying at least a portion of base means 11 provides a protective resilient layer 14 over tip portion 8 of surgical instrument 5 for protecting a user against injury due to contact with instrument tip portion 8 while handling the device, as is best seen in FIGS. 2 and 5.

In the exemplary embodiment of the present invention, the protective resilient layer 14 is formed of an opaque reticulated material which has a sufficient coarse pore size to allow visual inspection of the instrument tip, as may be seen in FIG. 5. A convenient, commercially available reticulated foam material on the order of 0.250 inches thick and having a pore size on the order of about ten pores per lineal inch has been found to be satisfactory for the purposes of this invention. A diagramatic representation of the relationship between the coarse pore material 21 of the protective resilient layer 14 and the fine pore material 22 of base means 11 is shown in FIG. 7. An open-cell reticle 20 is also shown.

It should be noted that in providing a protective resilient layer 14 of reticulated foam material on the order of 0.250 inches thick, the pouch 19 allows the nurse to firmly grasp the pouch 19 of surgical instrument holder and instrument tip protector device 10 with the heels of the hands without risking contamination of the instrument tip as would occur should the instrument contact the nurse's hands or puncture the surgical gloves being worn by the nurse. Further, the nurse may handle the device without risking injury from the enclosed surgical instrument as it is withdrawn from the device by the surgeon or physician. The protective resilient layer 14 pads and cushions the instrument tip portion 8, prevents contact between the instrument portion 8 and the nurse's hands, and provides a non-skid, non-slipping retention of the surgical instrument 5 until withdrawn from the device by the surgeon or physician.

In applications requiring maximum protection, when the tip portion of the surgical instrument deviates from the general plane of the handles, such as occurs with curved hemostats, forceps, scissors, or knives, a layer 211a of base means 211 may be extended over and attached to at least a portion of protective means 214. This will provide a zone of laminar structure forming pouch 219 comprising a layer of resilient protective material 214 bonded to a layer of base material 211a. This laminar structure overlying a portion of base 211 forms a reinforced pouch 219 which is extremely resistant to punctures by instrument tip portions. This embodiment of the present invention is shown best in FIG. 8.

It should be noted that there may be a sufficient portion of protective layer means 214 which is not overlayed with base means 211a to enable a user to visually inspect the instrument tip.

A further safety and aseptic advantage of the protective device of the present invention is that it prevents the instrument tip portion 8 from accidentially puncturing or cutting sterile envelope 1 during handling.

As may be readily observed, the provision of an individual pouch 19 coupled with holding slots 12 and 12a prevents surgical instrument 5 from moving from a position of alignment with respect to surgical instrument holder and instrument tip protector device 10 which is retained within sterile envelope 1. This results in a restriction of movement of surgical instrument 5 with respect to sterile envelope 1.

Once sterile envelope 1 has been opened, the surgical instrument holder and instrument tip protector device 10 may also function as a support and a holder for surgical instrument 5, as shown in FIGS. 3 and 5.

Exemplary of a further advantage of the present invention is an embodiment shown in FIGS. 3 and 4. A plurality of base means 11 and protective resilient layer means 14 are formed into a plurality of surgical instrument holder and tip protector devices in side-by-side integral relation for use together. Additionally, as best seen in FIG. 4, the devices 10 may be separated along zones 115 into individual sections for use.

In order to form the plurality of base means and protective resilient layer means in side-by-side integral relation, protective resilient layer means 114 is periodically sealed at zones shown at 115 against base means 111 to form a plurality of individual side-by-side pouches 119, each to receive the tip portion 8 of each of a plurality of surgical instruments 45. Again, as was discussed prior, and as may be seen in FIG. 4, instrument holding slots 112a, 112b, 112c and 112d are formed in spaced locations integrally with base 111 and are aligned to individual pouches 119 for holding each individual one of the plurality of instruments aligned with its associated surgical instrument holder and instrument tip protector device 110.

The exemplary embodiments thus far discussed in surgical instrument holder and instrument tip protector devices are formed of a sterilizable resilient opaque reticulated material. Polyurethane ester reticulated foam has been shown to be satisfactory in the use to which the surgical instrument holder and instrument top protector device of the present invention is applied. This material has been shown to be sterilizable by steam, to withstand temperatures of up to 350° F., to be impervious to ethylene oxide sterilizing gas (ETO), to be non-absorbent, to dry quickly with no moisture retention, and to contain no plasticizer which might outgas and form a toxic residue on surgical instruments during heat sterilization in an autoclave. Exemplary of acceptable sterilizable resilient material which has the further attributes of being opaque, reticulated, and inert during sterilization is SCOTT INDUSTRIAL FOAM, which is described as "a reticulated, fully open-pore, flexible, ester type of polyurethane foam. It is characterized by a patented three-dimensional structure of strands which provide a constant 97% of void space and a very high degree of permeability". This material is available from the Foam Division, SCOT PAPER COMPANY, 1500 East Second Street, Chester, Pennsylvania 19013.

In practicing the improvement in surgical instrument holder and instrument tip protector devices of the present invention, it has been found that foam having on the order of 60 pores per lineal inch is satisfactory for base means 11. Foam material having a pore size of on the order of 10 pores per lineal inch has been found to be satisfactory for protective resilient layer 14 as it is sufficiently coarse to allow visual inspection therethrough of the instrument tip covered thereby and also pad and protect tip portion 8 of a surgical instrument.

Referring now to FIG. 9, an alternative exemplary embodiment of surgical instrument holder and instrument tip protector device is indicated generally at 210 which is constructed generally as the device indicated generally at 110 in FIG. 4. As in the prior embodiment, the plurality of instrument tip protecting pouches 219 are formed of the aforedescribed protective resilient layer means as layer 114 in the prior embodiment. However, in the present embodiment, each individual device, to be divided along the cutlines 215, is also provided with one or more loops 212a and 212b for retaining a protective instrument thereon. These loops 212a, 212b are preferably made of the same opaque reticulated material as is used for forming the individual pouches 219.

Figure 11:
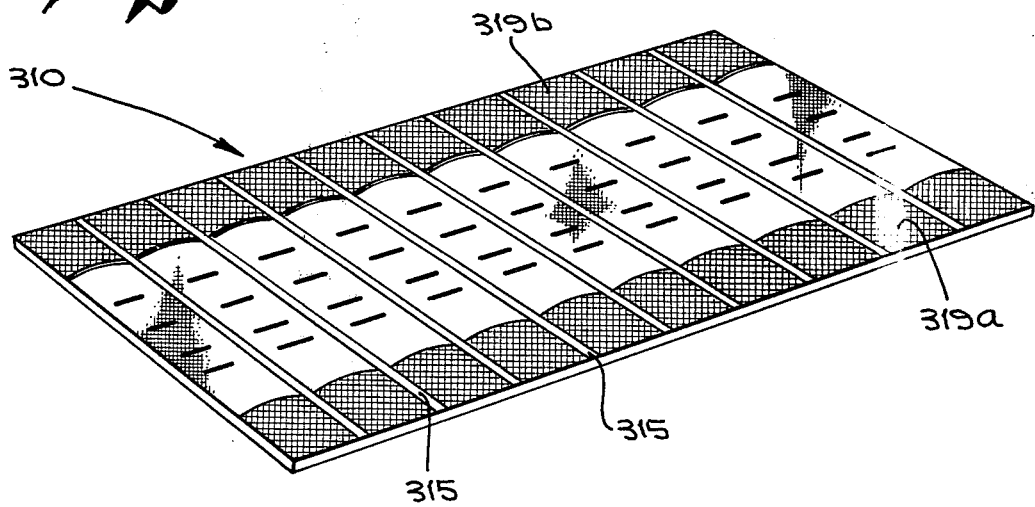
FIG. 11 is a plan view of a still further exemplary embodiment of the surgical instrument holder and instrument tip protector device of the present invention.

A further alternative embodiment of the present invention is shown in FIG. 11 generally at 310. However, in this embodiment, each of the individually separable instrument holder and instrument tip protector devices, separated along the cutlines 315, is provided with a protective pouch 319a not only at the lower end, as seen in FIG. 11, but also an identical pouch 319b at the upper end. Through such provision of protective pouches, according to the present invention, at either end of the holder base, the opposite ends of a surgical instrument may be protected against damage or injury to the user. It has been found that in holding surgical instruments, such as glass syringes, such double ended pouch construction of the present invention provides a better instrument holder than heretofore available. This is particularly true with reusable glass syringes which need to be protected against breakage.

Figure 10:
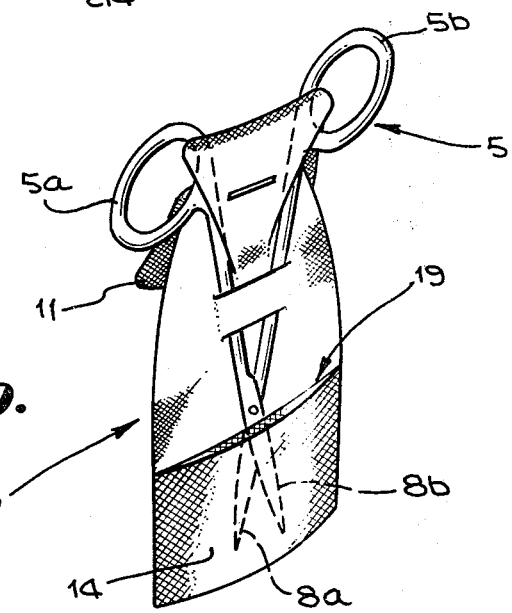
FIG. 10 is a view of the device of FIGS. 1 through 8 showing a surgical instrument in hold open position ready to be sterilized with the instrument tips within the protective pouch.

Referring now to FIG. 10, the exemplary embodiment of instrument holder and instrument tip protector device of FIGS. 1 through 8 is illustrated in a position of use suitable for sterilizing the held instrument. As seen in FIG. 10, the holder device, indicated generally at 10 is shown with its base means 11 doubled back and pushed between the open handle ends 5a and 5b of a surgical scissors 5. Scissors tip portions 8a and 8b are thus held in open position, particularly suited for sterilization, within the protective pouch 19 formed by the protective resilient layer 14. The surgical instrument holder and instrument tip protector device of the present invention is therefore ideally suited for holding surgical instrument having separable parts in an open condition whereby a greater surface area of the instrument parts can be sterilized through the holder, as seen in the example of FIG. 10. Further, the pouch construction of the present invention allows the opening of the surgical instrument tips within the pouch, while maintaining the protective function of the pouch outer layer 14.

Although this invention is improved surgical instrument holder and instrument tip protector devices has been described in detail, with particular reference to certain exemplary embodiments, it is to be understood that various modifications thereof can be made by one skilled in the art, and still come within the scope and spirit of the present invention which is only limited as defined by the following claims.

I claim:

1. A surgical instrument holder and instrument tip protector device comprising:
    base means of a sterilizable reticulated material having a substantially fine pore size for receiving a surgical instrument positioned thereon; and
    an open ended protective pouch means formed of a sterilizable reticulated foam material having a substantially coarse pore size relative to said base pore size to allow visual inspection therethrough and overlying and peripherally bonded to only a portion of said base, which portion covers a tip only of the instrument, for providing an instrument tip receiving open ended pounch said pouch having an open space therewith into which a tip end of said instrument may be removably positioned while allowing sterilization and visual inspection of said instrument therethrough, and at least one loop on said base aligned with said pouch opening to hold said instrument thereon.

2. The device of claim 1 wherein said protective means is formed of an opaque reticulated material having a substantially coarse pore size on the order of about ten pores per lineal inch to allow visual inspection and identification of the instrument tip covered thereby.

* * * * *